United States Patent
Krich et al.

(10) Patent No.: US 6,894,170 B2
(45) Date of Patent: May 17, 2005

(54) PROCESS FOR THE PREPARATION OF SUBSTITUTED THIAZOLINES AND THEIR INTERMEDIATES

(75) Inventors: Sylvia Krich, Altenberg b. Linz (AT); Alexander Rieder, Kundl (AT); Ferdinand Heu, Linz (AT); Gerhard Steinbauer, Enns (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 0 days.

(21) Appl. No.: 10/270,324

(22) Filed: Oct. 15, 2002

(65) Prior Publication Data

US 2003/0088105 A1 May 8, 2003

(30) Foreign Application Priority Data

Oct. 16, 2001 (AT) ........................ A 1639/2001

(51) Int. Cl.⁷ ............................................. C07D 277/10
(52) U.S. Cl. ............................................. 548/201
(58) Field of Search ....................................... 548/201

(56) References Cited

U.S. PATENT DOCUMENTS

2003/0220504 A1 * 11/2003 Chorghade et al. ......... 548/201

OTHER PUBLICATIONS

Provisional application 60/381021, May 15, 2002.*
Mulqueen et al., *Tetrahedron*, vol. 49, No. 24, pp. 5359–5364, (1993).
Ehrler et al, *Synlett*, pp. 702–703, (1994).

* cited by examiner

*Primary Examiner*—Laura L. Stockton
(74) *Attorney, Agent, or Firm*—Wenderoth, Lind & Ponack, L.L.P.

(57) ABSTRACT

Process for the preparation of substituted thiazolines of the formula (I)

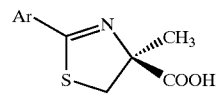

in which Ar is a phenyl, naphthyl, thienyl, pyridyl or quinolinyl radical which can optionally be substituted by one or more substituents from the group consisting of halogen, OH, benzyloxy, $C_1$–$C_4$-alkyl, $C_1$–$C_4$-alkoxy, $COOR_1$ where $R_1$ is H or $C_1$–$C_4$-alkyl, by coupling of (S)-α-methylcysteine hydrochloride of the formula (II)

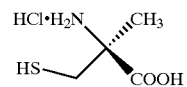

with a nitrile of the formula (III)

Ar—CN in which Ar is as defined above, or a corresponding $C_1$–$C_4$-alkyl imidate, in which (S)-α-methylcysteine hydrochloride of the formula (II) is reacted in a suitable solvent with a nitrile of the formula (III) or a corresponding $C_1$–$C_4$-alkyl imidate in the presence of a tertiary base at a pH of 6.5 to 10 at 50° C. up to the reflux temperature to give the corresponding thiazoline of the formula (I), and processes for the preparation of (S)-α-methylcysteine hydrochloride and its use for the preparation of thiazolines of the formula (I).

3 Claims, No Drawings

PROCESS FOR THE PREPARATION OF SUBSTITUTED THIAZOLINES AND THEIR INTERMEDIATES

Substituted thiazolines, such as, for example, 4,5-dihydro-2-(2,4-dihydroxyphenyl)-4-methylthiazole-4-(S)-carboxylic acid, 4,5-dihydro-2-(2,3-di-hydroxyphenyl)-4-methylthiazole-4-(S)-carboxylic acid, 4,5-dihydro-2-(2-hydroxy-3-methoxyphenyl)-4-methylthiazole-4-(S)-carboxylic acid, 4,5-dihydro-2-(4-carboxy-2-hydroxyphenyl)-4-methylthiazole-4-(S)-carboxylic acid, 4,5-dihydro-2-(2-hydroxyphenyl)-4-methylthiazole-4-(S)-carboxylic acid, 4,5-dihydro-2-(3-hydroxyquinolin-2-yl)-4-methylthiazole-4-(S)-carboxylic acid, 4,5-dihydro-2-(2-hydroxynaphth-1-yl)-4-methylthiazole-4-(S)-carboxylic acid, 4,5-dihydro-2-(3-hydroxynaphth-2-yl)-4-methylthiazole-4-(S)-carboxylic acid, 4,5-dihydro-2-(2-hydroxyphenylmethyl)-4-methylthiazole-4-(S)-carboxylic acid, etc. are potential iron chelators. The preparation of these compounds is carried out via the coupling of (S)-α-methylcysteine or of a salt thereof with the appropriate nitrile or imidoester compound and has already been described in the literature. Thus, the coupling of (S)-α-methylcysteine hydrochloride with 2,4-dihydroxybenzonitrile is carried out, for example, according to J. Med. Chem. 1999, 42, 2432–2440 in degassed methanol by heating at 71° C. for 3 days with addition of degassed phosphate buffer to achieve a pH of 6, whereby, after working up the reaction mixture, 4,5-dihydro-2-(2,4-dihydroxyphenyl)-4-methylthiazole-4-(S)-carboxylic acid is obtained in 57% yield. Analogously, 4,5-dihydro-2-(2-hydroxyphenyl)-4-methylthiazole-4-(S)-carboxylic acid is prepared in a yield of only 32%. An important intermediate compound for the synthesis of the abovementioned target compounds is in this case (S)-α-methylcysteine, which is obtained, for example, according to Tetrahedron 1993, 49 (24), 5359–5364 in a Seebach-analogous synthesis by acidic hydrolysis of 2S,4S-methyl 2-tert-butyl-1,3-thiazolidine-3-formyl-4-methyl-4-carboxylate. 2S,4S-Methyl 2-tert-butyl-1,3-thiazolidine-3-formyl-4-methyl-4-carboxylate is in this case prepared starting from (S)-cysteine methyl ester and pivaldehyde via 2S-methyl 2-tert-butyl-1,3-thiazolidine-4-carboxylate, introduction of a formyl protective group to give 2S,4S-methyl 2-tert-butyl-1,3-thiazolidine-3-formyl-4-carboxylate, reaction at −78° C. with lithium diisopropylamide to give the corresponding enolate and quenching of the enolate with methyl iodide. The yield of (S)-α-methylcysteine starting from (S)-cysteine methyl ester is in this case only 29%. In addition to the low yield of (S)-α-methylcysteine, the laborious process steps and especially the starting material (S)-cysteine methyl ester hydrochloride, a compound which is unnatural, commercially unavailable and therefore not to be taken into consideration for industrial syntheses, are significant disadvantages of this preparation variant.

In Synlett (1994), page 702–703, (R)- and (S)-methylcysteine ethyl ester hydrochloride are prepared by reaction of ethyl benzimidate hydrochloride with L-cysteine ethyl ester hydrochloride, subsequent methylation and resolution of the racemic mixture of 4-carbethoxy-4-methyl-2-phenylthiazoline obtained thereby by means of preparative HPLC on cellulose triacetate, and acidic hydrolysis of the enantiomerically pure (R) and (S)-4-carbethoxy-4-methyl-2-phenylthiazolines with subsequent esterification. (R)-Methylcysteine ethyl ester hydrochloride is then condensed with cyanomethyl diphenylphosphine oxide to give the corresponding thiazoline. In the further sequence, according to Synlett, thiangazole is prepared as a final product.

It was an object of the invention to find a process which can be carried out on an industrial scale which guarantees the preparation of substituted thiazolines in higher yields in comparison with the prior art combined with simpler implementation of the reaction.

The invention therefore relates to a process for the preparation of substituted thiazolines of the formula (I)

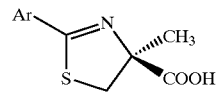

in which Ar is a phenyl, naphthyl, thienyl, pyridyl or quinolinyl radical which can optionally be substituted by one or more substituents from the group consisting of halogen, OH, benzyloxy, $C_1$–$C_4$-alkyl, $C_1$–$C_4$-alkoxy, $COOR_1$ where $R_1$ is H or $C_1$–$C_4$-alkyl, by coupling of (S)-α-methylcysteine hydrochloride of the formula (II)

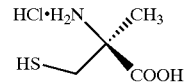

with an aromatic or heteroaromatic nitrile of the formula (III)

in which Ar is as defined above or a corresponding $C_1$-$C_4$-alkyl imidate, which comprises reacting (S)-α-methylcysteine hydrochloride of the formula (II) in a $C_1$–$C_4$-alcohol, a mixture of two or more $C_1$–$C_4$-alcohols or a mixture of $C_1$–$C_4$-alcohol and a hydrocarbon containing 0.5 to 2 mol of a nitrile of the formula (III) or a corresponding $C_1$–$C_4$-alkyl imidate per mole of (S)-α-methylcysteine hydrochloride in the presence of 1.5 to 3 mol of a tertiary base per mole of (S)-α-methylcysteine hydrochloride at a pH of 6.5 to 10 at 50° C. up to the reflux temperature to give the corresponding thiazoline of the formula (I), which is isolated from the reaction mixture by removal of the solvent, extraction of the impurities and precipitation of the thiazoline by acidification.

By means of the process according to the invention, substituted thiazolines of the formula (I) are prepared.

In the formula (I), Ar is a phenyl, naphthyl, thienyl, pyridyl or quinolinyl radical, the phenyl and naphthyl radical being preferred. Particularly preferably, Ar is phenyl.

The radicals can in this case optionally also be mono- or polysubstituted by substituents from the group consisting of halogen, such as fluorine, chlorine, iodine or bromine, OH, benzyloxy, $C_1$–$C_4$-alkyl, such as methyl, ethyl, propyl and butyl, $C_1$–$C_4$-alkoxy, such as methoxy, ethoxy, butoxy, $COOR_1$ where $R_1$ is H or $C_1$–$C_4$-alkyl. Preferred substituents are Cl, OH, methyl, methoxy and COOH; OH is particularly preferred.

Preferably, Ar is substituted by one or two, particularly preferably by two, of the abovementioned substituents.

Possible preferred final compounds which can be prepared according to the invention are, for example, 4,5-dihydro-2-(2,4-dihydroxyphenyl)-4-methylthiazole-4-(S)-carboxylic acid, 4,5-dihydro-2-(2,3-dihydroxyphenyl)-4-methylthiazole-4-(S)-carboxylic acid, 4,5-dihydro-2-(2-hydroxy-3-methoxyphenyl)-4-methylthiazole-4-(S)-carboxylic acid, 4,5-dihydro-2-(4-carboxy-2-hydroxyphenyl)-4-methylthiazole-4-(S)-carboxylic acid, 4,5-dihydro-2-(2-hydroxyphenyl)-4-methylthiazole-4-(S)-carboxylic acid, 4,5-di-hydro-2-(3-hydroxyquinolin-2-yl)-4-methylthiazole-4-(S)-carboxylic acid, 4,5-dihydro-2-(2-hydroxynaphth-1-yl)-4-methylthiazole-4-(S)-carboxylic acid, 4,5-dihydro-2-(3-hydroxynaphth-2-yl)-4-methylthiazole-4-(S)-carboxylic acid, 4,5-dihydro-2-(2-hydroxyphenylmethyl)-4-methylthiazole-4-(S)-carboxylic acid, etc.

As starting compounds, (S)-α-methylcysteine hydrochloride of the formula (II) and a nitrile of the formula (III) or a corresponding imidate are employed.

(S)-α-Methylcysteine hydrochloride can be prepared, for example, according to the prior art, such as, for example, according to Synlett (1994), pages 702–703. Preferably, (S)-α-methylcysteine hydrochloride, however, is prepared according to a modified variant, to which the invention likewise relates.

In this modified variant, in the first stage L-cysteine compounds of the formula (IV)

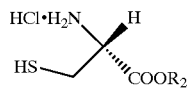

in which $R_2$ is H or $C_1$–$C_4$-alkyl, are coupled to optionally substituted nitriles of the formula (V)

in which Ar is a phenyl, naphthyl, thienyl, pyridyl or quinolinyl radical which can optionally be substituted by one or more substituents from the group consisting of halogen, OH, benzyloxy, $C_1$–$C_4$-alkyl, $C_1$–$C_4$-alkoxy, $COOR_1$ where $R_1$ is H or $C_1$–$C_4$-alkyl, where the OH groups can optionally be protected by a suitable protective group, such as, for example, tetrahydropyranyl, acetyl, benzyl etc., or a corresponding $C_1$–$C_4$-alkyl imidate, in the presence of a tert-base, such as triethylamine, di-i-propylethylamine, pyridine, etc. in a $C_1$–$C_4$-alcohol, such as methanol, ethanol, butanol, a mixture of two or $C_1$–$C_4$-alcohols or a mixture of $C_1$–$C_4$-alcohol and a hydrocarbon, such as, for example, toluene, or an alkane, e.g. hexane, heptane etc., to give a compound of the formula (VI)

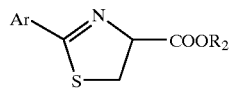

in which Ar and $R_2$ are as defined above.

Suitable L-cysteine compounds of the formula (IV) are L-cysteine, and the L-cysteine $C_1$–$C_4$-ester hydrochlorides.

The L-cysteine compound of the formula (IV) is then reacted either with an appropriate nitrile of the formula (V) or the corresponding $C_1$–$C_4$-alkyl imidate·HCl.

Suitable nitriles in this case are benzonitrile, tolunitrile or 2,4-dihydroxybenzonitrile protected on the oxygen atoms, for example by tetrahydropyranyl, acetyl or benzyl.

The corresponding $C_1$–$C_4$-alkyl imidates are either commercially obtainable or can be prepared from the nitriles using a $C_1$–$C_4$-alcohol and HCl.

The nitrile of the formula (V) or the corresponding alkyl imidate is in this case preferably employed in an equimolar amount based on the L-cysteine compound of the formula (IV). If appropriate, an excess can also be employed, whereby, however, no advantages are achieved. The coupling with the L-cysteine compound is carried out in the presence of a tert-base, such as triethylamine, di-i-propylethylamine or pyridine. Preferably, triethylamine is used.

The tert-base is added in an amount from 0.9 to 1.3 mol, preferably from 1.0 to 1.2 mol and particularly preferably from 1.02 to 1.1 mol, per mole of L-cysteine compound.

Greater excesses can also be employed, but have a negative effect on the yield.

Compounds of the formula (VI) are, for example, 4-carbethoxy-2-phenylthiazoline, 2-phenylthiazoline-4-carboxylic acid, 4-carbethoxy-2-(2,4-di-tetrahydropyranyl)thiazoline, etc.

If L-cysteine is employed as the L-cysteine compound, a compound of the formula (VI) is obtained where $R_2$ is H, which is then converted into a $C_1$–$C_4$-ester.

The compound of the formula (VI) in which $R_2$ is $C_1$–$C_4$-alkyl is then reacted in a 2nd stage, after aqueous work-up and extraction, if appropriate azeotropic drying of the extracts and/or if appropriate isolation of the compound, with a methylating reagent, for example with methyl iodide, chloride or bromide, under the action of a base to give the corresponding thiazoline of the formula (VII)

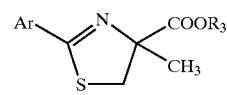

in which Ar is as defined above and $R_3$ is $C_1$–$C_4$-alkyl, such as, for example, 4-carbethoxy-4-methyl-2-phenylthiazoline or 4-carbethoxy-4-methyl-4-(2,4-ditetrahydropyranyl)thiazoline etc.

This 2nd step is carried out in an ether, for example methyl tert-butyl ether (MTBE), tetrahydrofuran (THF) or diethyl ether, and in the presence of a base. The base used is preferably lithium diisopropylamide (LDA), which is obtained from diisopropylamine and butyllithium.

The methylating agent is employed here in an amount from 1 to 3 mol, preferably from 1 to 2 mol and particularly preferably from 1.2 to 1.7 mol per mole of compound of the formula (VI).

LDA is employed in an amount from 1 to 1.5 mol, preferably from 1 to 1.3 mol and particularly preferably from 1.05 to 1.2 mol per mole of compound of the formula (VI).

The methylation is carried out at a temperature from −80° C. to +40° C., preferably from −30° C. to +35° C. and particularly preferably from −20° to +30° C.

After reaction has taken place, sufficient HCl is added such that a pH of between 1.5 and 5, preferably between 2 and 3, is achieved, whereupon a two-phase mixture is obtained.

The organic phase, which contains the thiazoline of the formula (VII), can be employed directly in the next phase, after extraction. The thiazoline of the formula (VII), however, can also firstly be isolated.

In the 3rd stage, by means of basic hydrolysis, and, if appropriate, after removal of a protective group on one or more hydroxyl group(s) located on the aromatic radical, the corresponding thiazolinecarboxylic acid of the formula (VIII)

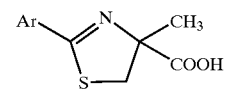

in which Ar is as defined above, such as, for example, optionally substituted 4-methyl-2-phenylthiazoline-4-carboxylic acid etc., is obtained as a racemate. This is carried out by addition of a base, such as, for example, NaOH, KOH, LiOH etc., or a mixture of base and THF or dioxane, preferably to the product solution from stage 2, whereby a two-phase reaction mixture is obtained, which is stirred at reflux temperature. After cooling to room temperature, the aqueous phase is treated with HCl until a pH of between 1.5 and 4.5, preferably between 1.5 and 4 and particularly preferably from 1.5 to 3, is achieved. By rendering acidic, the acid separates as an oil, which can optionally be further isolated by extraction, separation of the organic phase, removal of water by azeotropic distillation and removal of the extracting agent by distillation.

As a 4th step, resolution with a cleavage base takes place. Suitable cleavage bases are, for example, enantiomerically pure, chiral amines, such as, for example, optionally substituted phenylethylamine, optionally substituted phenylglycinamide, norephedrine, quinine, etc.

The cleavage is carried out in a solvent in which the thiazoline-4-carboxylic acid of the formula (VIII) dissolves, for example in an alcohol, such as, for example, ethanol, propanol, etc., an alcohol/water mixture, an acetic acid ester, such as, for example, isopropyl acetate (IPA), ethyl acetate, etc. After the addition of the cleavage base, the crystallization is begun by cooling the reaction mixture with stirring. To this end, for example, a multistage temperature program in which the cooling rate varies in the individual stages can be chosen. In the case of the crystallization, it is also possible to assist or induce this by seeding. Preferably, after the seeding, cooling is carried out somewhat more slowly for a time and, toward the end of the crystallization, for complete precipitation, cooling is again carried out somewhat more rapidly. The cooling is carried out from room temperature down to −15° C. After crystallization is complete, the mixture is filtered, and the crystals are preferably washed and then optionally dried.

The salts of the carboxylic acid thus obtained are then preferably recrystallized for purification. To this end, the crystals obtained are dissolved in a suitable solvent at elevated temperature and the purified carboxylic acid salt is in turn crystallized out by cooling with stirring. Here too, a multistage temperature program is possible.

After crystallization has finished, the corresponding chiral carboxylic acid salt is in turn filtered off and optionally dried.

For the release of the corresponding chiral acid, HCl is then added to a mixture of chiral salt, water and a suitable solvent, whereby two clear phases are obtained. Suitable solvents are those which are not miscible with water, which dissolve the acid and which are resistant to HCl. Examples of these are ethers or esters. Preferably, ethers are employed, particularly preferably MTBE. The HCl addition takes place until the pH of the aqueous phase is 1 to 4, preferably 1 to 3 and particularly preferably 1.5 to 3. The organic phase is then separated off and optionally washed. After separation of the solvent, the (S)-thiazolinecarboxylic acid of the formula (VIII), for example (S)-4-methyl-2-phenylthiazoline-4-carboxylic acid or (S)-4-methyl-2-(2,4-dihydroxyphenyl) thiazoline-4-carboxylic acid etc. is obtained.

Instead of the resolution by cleavage bases, however, a lipase-catalysed resolution of the thiazoline of the formula (VII) can also be carried out.

Suitable lipases are, for example, pig liver esterase, *Candida rugosa* lipase, *Aspergillus* species lipase, *Aspergillus* species protease, *Bacillus* species protease, subtilisin Carlsberg, *Candida antarctica* "A" lipase, *Candida antarctica* "B" lipase, ChiroCLEC$_{TM-PC}$ (dry), ChiroCLEC$_{TM-PC}$ (slurry), etc.

The (S)-thiazolinecarboxylic acid of the formula (VIII) is converted into (S)-2-methylcysteine·HCl in the further sequence by acidic hydrolysis.

To this end, the (S)-thiazolinecarboxylic acid of the formula (VIII) is dissolved in HCl and the solution thus obtained is boiled at reflux temperature. Preferably, the reaction is in this case carried out under a nitrogen atmosphere. After 1 to 30 hours, preferably 5 to 25 hours and particularly preferably after 10 to 20 hours, the reaction mixture is cooled to 0 to 35° C., preferably to 10 to 30° C. and particularly preferably to 10 to 20° C. and the precipitated cleavage product, for example optionally substituted benzoic acid, is separated off, which is then washed one or more times with optionally degassed water or with dilute HCl. The acidic filtrate is optionally firstly extracted with a suitable extracting agent for the complete removal of the cleavage product. Examples of suitable solvents are MTBE, toluene, ethyl methyl ketone, IPA, THF, CH$_2$Cl$_2$, diethyl ether etc. The isolation of (S)-2-methylcysteine·HCl can then be carried out by means of spray drying of the aqueous phase. In another variant, the aqueous phase is evaporated, preferably under reduced pressure, whereby an oil is obtained, which in the further sequence is dissolved 1 to 5 times in optionally degassed water, or a mixture of water with tetrahydrofuran (THF), acetone or IPA, and in each case is evaporated completely or to a 65 to 20% strength solution, preferably under reduced pressure.

If the reaction mixture is not completely evaporated, a solvent suitable for the azeotropic distillation, which forms an azeotrope with water, for example toluene, dichloromethane, 2-butanol, i-propanol or MTBE, is added to the concentrated solution thus obtained and the water contained in the solution is removed by entrainment. The residual suspension or solution, which contains the (S)-2-methylcysteine·HCl, can then be employed directly in the next stage, the coupling with a nitrile of the formula (III). If appropriate, to this end the solution or suspension is made up with fresh solvent and then reacted directly with the nitrile of the formula (III) in the presence of a tertiary base to give the desired final product, a thiazoline of the formula (I).

The residual suspension or solution, however, can also optionally be treated with an ether, such as, for example, MTBE, diethyl ether, diisopropyl ether, etc., or a hydrocarbon, such as, for example, a C$_6$–C$_8$-alkane, toluene, etc., to precipitate the (S)-2-methylcysteine·HCl, whereupon the (S)-2-methylcysteine·HCl is filtered off, washed one or more times with the ether or hydrocarbon used and dried in vacuo.

By means of this method according to the invention, (S)-2-methylcysteine·HCl is obtained in crystalline form in a yield of up to 95%.

A further process variant according to the invention for (S)-2-methylcysteine·HCl is a modified variant of the Seebach-analogous synthesis described in Tetrahedron (1993), 49 (24), pp. 5359–5364, which is based on the enantioselective methylation, induced by a chiral protective group, of the unnatural and therefore commercially unavailable (S)-2-methylcysteine ester·HCl.

In the variant according to the invention, the readily available L-cysteine ethyl ester·HCl is reacted in a first stage with 2 to 3 equivalents of acetone in a hydrocarbon, for example toluene, hexane, etc. or in acetone itself, if appropriate in the presence of a tert-amine, such as triethylamine, di-i-propylethylamine or pyridine etc. After the separation of the water of reaction, the reaction mixture is cooled, the precipitate is filtered off, optionally washed and the filtrate is freed of the solvent. If acetone itself is employed as the solvent, the separation of the water of reaction is unnecessary. The reaction solution is only concentrated, the residue is partitioned between NaHCO$_3$, NaOH or KOH and toluene and the product is isolated from the organic phase.

The acetonide thus obtained is dissolved in 2 to 3 equivalents of formic acid in the 2nd stage, treated with toluene or acetic anhydride and the reaction mixture obtained is stirred for some time, preferably for 10 min up to 5 hours. The reaction mixture is then concentrated and partitioned between an ether, ester or suitable hydrocarbon and a sodium hydrogencarbonate, NaOH or KOH solution. The organic phase is azeotropically dried and freed of the solvent.

In the 3rd stage, the methylation of the N-formylated acetonide (ethyl 3-formyl-2,2-dimethylthiazoline-4- carboxylate) obtained from the 2nd stage is carried out by deprotonation using 1 to 1.5 equivalents, preferably from 1.1 to 1.2 equivalents, of LDA and subsequent reaction with 1 to 2 equivalents, preferably with 1.1 to 1.5 equivalents, of methylating agent.

Suitable solvents are, for example, MTBE, THF, diethyl ether, etc. If appropriate, a cosolvent, such as, for example, 1,3-dimethyl-3,4,5,6-tetrahydro-(1H)-pyrimidinone (DMPU) can also be added. The reaction temperature is −25 to −80° C., preferably −35 to −75° C. and particularly preferably −45 to −55° C. An aqueous work-up is then carried out.

The separation of enantiomers of the racemic ethyl 3-formyl-2,2,4-trimethylthiazoline-4-carboxylate is then preferably carried out by means of selective ester hydrolysis using a lipase, for example using pig liver esterase, *Candida rugosa* lipase, *Aspergillus* species lipase, *Aspergillus* species protease, *Bacillus* species protease, subtilisin Carlsberg, *Candida antarctica* "A" lipase, *Candida antarctica* "B" lipase, ChiroCLEC$_{TM-PC}$ (dry), ChiroCLEC$_{TM-PC}$ (slurry), etc.

After separation of enantiomers has taken place, in the 5th stage the hydrolysis to (S)-2-methylcysteine·HCl is carried out analogously to the process described previously, the separation of the benzoic acid being unnecessary.

The (S)-2-methylcysteine·HCl prepared according to the prior art or preferably the (S)-2-methylcysteine·HCl prepared according to one of the variants according to the invention, preferably according to the modified Synlett variant, is then coupled to an aromatic or heteroaromatic nitrile of the formula Ar—CN (III) or a corresponding $C_1$–$C_4$-alkyl imidate.

In the formula (III), Ar has the same meaning as in formula (I).

The nitriles are in some cases purchasable, but can also be prepared from the corresponding aldehydes, for example by means of formic acid, sodium formate and hydroxylammonium sulfate.

The corresponding $C_1$–$C_4$-alkyl imidates can be prepared from the nitrites using a $C_1$–$C_4$-alcohol and HCl.

The appropriate nitrile or the imidate is then coupled according to the invention with (S)-2-methylcysteine·HCl.

The coupling is carried out in a $C_1$–$C_4$-alcohol, a mixture of two or more $C_1$–$C_4$-alcohols or a mixture of $C_1$–$C_4$-alcohol and a hydrocarbon containing 0.5 to 2 mol of a nitrile of the formula (III) or to the corresponding $C_1$–$C_4$-alkyl imidate per mole of (S)-α-methylcysteine hydrochloride in the presence of 1.5 to 3 mol of a tertiary base per mole of (S)-α-methylcysteine hydrochloride. Preferably, 0.8 to 1.5 mol, particularly preferably 0.9 to 1.1 mol, of nitrile or imidate are employed. Suitable tert-bases are, for example, triethylamine, di-i-propylethylamine or pyridine, which are preferably added in an amount of 1.8 to 2.5 mol, particularly preferably 1.9 to 2.2 mol, of amine per mole of (S)-α-methylcysteine hydrochloride. Suitable solvents are $C_1$–$C_4$-alcohols, such as methanol, ethanol, butanol, a mixture of two or more $C_1$–$C_4$-alcohols or a mixture of $C_1$–$C_4$-alcohol and a hydrocarbon, such as, for example, toluene, $C_6$–$C_8$-alkane, etc. Preferably, however, ethanol and/or butanol are/is employed.

By means of the addition of the tert-base, a pH of 6.5 to 10, preferably of 7 to 9 and particularly preferably of 7.5 to 8, is established in the reaction solution. The reaction mixture is heated to 50° C. up to the reflux temperature with stirring for 1 to 40 hours, preferably for 5 to 30 hours and particularly preferably for 15 to 25 hours, preferably under a nitrogen atmosphere.

The mixture is then optionally cooled and the solvent is distilled off, preferably under reduced pressure, whereby an oil is obtained.

The corresponding thiazoline of the formula (I) is then isolated from this oil by extraction of the impurities from the reaction mixture and precipitation of the thiazoline by acidification.

To this end, the oil is partitioned between water and a suitable solvent or extracting agent and excess starting material is extracted at a suitable pH. For example, when using 2,4-dihydroxybenzonitrile, the oil is taken up in water, the pH is adjusted to a pH of 6.5 to 9, preferably of 7 to 9 and particularly preferably of 7.5 to 8 using a suitable base, for example using KOH, NaOH, etc. and extracted one or more times using a suitable extracting agent, such as, for example, diethyl ether, MTBE, dichloromethane, ethyl acetate, etc.

The aqueous phase is separated off and adjusted to a pH of 10 to 14, preferably of 11 to 13, using a suitable base, for example using KOH, NaOH, etc. Extraction one or more times is then carried out again using a suitable extracting agent, such as, for example, diethyl ether, MTBE, dichloromethane, ethyl acetate, etc. The mixture is then optionally filtered, for example using activated carbon, and then a pH of 6.5 to 10, preferably of 7 to 9 and particularly preferably of 7.5 to 8 is established using a suitable acid, such as, for example, HCl, $H_2SO_4$, HBr, etc. The extracting agent is then completely removed from the water phase by distillation, preferably under reduced pressure.

The extraction and purification steps at different pH can also be carried out in a different sequence.

The residual aqueous solution is acidified using a suitable acid, such as, for example, HCl, $H_2SO_4$, HBr, etc. until a pH of 1 to 3, preferably of 1 to 2, is achieved. During the course of this, the desired thiazoline begins to crystallize out. The suspension thus obtained is then stirred at a temperature of 5 to 25° C., preferably of 10 to 20° C., for some time, preferably for 10 min to 3 hours, particularly preferably for 30 min to 1.5 hours, then the solid is filtered off, washed and dried in vacuo.

By means of the coupling process according to the invention, thiazolines of the formula (I) are obtained in significantly higher yields of up to 99% in comparison with the prior art.

EXAMPLE 1

Preparation of (S)-2-methylcysteine·HCl

1st Stage: Coupling to 4-carbethoxy-2-phenylthiazoline 100 g (0.54 mol, 1.00 eq) of ethyl benzimidate·HCl and 100 g (0.54 mol, 1.00 eq) of cysteine ethyl ester·HCl were suspended in 500 ml of ethanol in a 500 ml Schmizo, equipped with a reflux condenser. The ethanol was degassed beforehand by heating it to reflux twice under a nitrogen atmosphere. After addition of 57.4 g (0.567 mol, 1.05 eq) of triethylamine, the reaction mixture was refluxed for 2 h. The ethanol was removed by distillation (455 ml of distillate) under reduced pressure (100 mbar), whereby an oily yellow suspension was obtained. 450 ml of MTBE were added to this. This mixture was washed with 200 ml of 0.5 M HCl and twice with 200 ml of water. The organic phase was separated off and the residual water was entrained by an azeotropic distillation (water separator, 4 h, 10 ml of water). A further 125 ml of MTBE were then removed by distillation in order to reduce the water content as far as possible. 400 ml of a pale yellow MTBE solution (water value according to Karl Fischer: <0.05% w/w) were obtained, which contains the product 4-carbethoxy-2-phenylthiazoline. This solution was employed in the 2nd stage.

2nd stage: Methylation to give 4-carbethoxy-4-methyl-2-phenylthiazoline 152.2 g (0.594 mol, 1.10 eq) of butyllithium solution (25% strength in heptane) were added dropwise under nitrogen in the course of 30 min to a solution of 90.8 ml (65.6 g, 0.648 mol, 1.20 eq) of diisopropylamine in 800 ml of absolute MTBE at −15° C. This solution was stirred at −15° C. for 30 min. 400 ml of the MTBE solution containing the 4-carbethoxy-2-phenyl-thiazoline were added dropwise at −15° C. in the course of 30 min and the mixture was stirred at −15° C. for 1 h, whereby a brown solution resulted. 115.0 g (50.4 ml, 0.81 mol, 1.50 eq) of methyl iodide were added and the reaction mixture was warmed to 23° C. and stirred at this temperature for a further 3 h. 300 ml of 2 M HCl were then slowly added with vigorous stirring, then the mixture was adjusted to pH 2–3 so that the temperature did not exceed 30° C. The two-phase mixture obtained thereby was stirred for a further 30 min. The organic phase was then separated off. This MTBE solution, containing 4-carbethoxy-4-methyl-2-phenylthiazoline, was employed in stage 3.

3rd stage: Basic hydrolysis to give rac. 4-methyl-2-phenylthiazoline-4-carboxylic acid 270 ml of 4 M NaOH (2 eq) were added to the product solution from stage 3 (1340 ml). This two-phase mixture was refluxed with stirring for 1 h (52° C. boiling temperature). After cooling to room temperature, the phases were separated. After removing ethanol from the aqueous phase by distillation under reduced pressure (50 mbar, 40° C., 100 ml of distillate), this was again washed with 250 ml of MTBE. The aqueous phase was separated off and adjusted to pH 2–3 using 6 M HCl, the temperature not exceeding 35° C. On rendering acidic, rac. 4-methyl-2-phenylthiazoline-4-carboxylic acid separated as an oil. In order to achieve a good phase separation, 100 ml of MTBE were added, the mixture was well shaken and the organic phase was separated off. The aqueous phase was washed with 200 ml of MTBE. The combined MTBE phases were washed with 100 ml of water. The water was then removed from the MTBE solution, which contained the acid, by means of azeotropic distillation. The MTBE was removed by distillation under reduced pressure at 50° C., whereby a brown oil was obtained. This was taken up once more in 200 ml of MTBE and MTBE was stripped off again until the racemic 4-methyl-2-phenylthiazoline-4-carboxylic acid had been obtained as an oil.

Total yield of stages 1–3: 92.9 g of racemic 4-methyl-2-phenylthiazoline-4-carboxylic acid (77.7% of theory)

4th Stage: Resolution using (R)-phenylethylamine via a diastereomeric salt

Crystallization:

92.9 g (0.42 mol, 1.00 eq) of the racemic 4-methyl-2-phenylthiazoline-4-carboxylic acid were dissolved in 370 ml of isopropyl acetate in a 500 ml Schmizo. 40.1 ml (38.2 g, 0.75 eq) of (R)-phenylethylamine were added to this suspension, a clear solution immediately being formed, using which the crystallization was carried out with stirring according to the following temperature program:
a.) in 30 min from room temperature to 15° C.;
b.) in 60 min from 15 to 10° C.;
c.) in 10 h from 10 to −10° C., stir at −10° C. overnight.

The solution was seeded with crystals of the phenylethylamine (PE) salt at 10° C. The crystallization commenced hereon at 7° C. After crystallization had finished, the mixture was filtered and the crystals were washed twice with 50 ml each of cold isopropyl acetate. The yellow PE salt was dried in vacuo at 50° C.

Yield: 48.0 g (33.4% of theory, ee %=91.5 (GC))

Recrystallization:

48.0 g (0.14 mol) of the PE salt were dissolved in 450 ml of isopropyl acetate in a 500 ml Schmizo at a jacket temperature of 90° C. A clear, yellowish solution was obtained, using which the recrystallization was carried out with stirring according to the following temperature program:
a.) in 2.5 h from 90 to 60° C.;
b.) in 4 h from 60 to 20° C.;
c.) in 10 h from 20 to −10° C., stir at −10° C. overnight.

The solution was seeded with crystals of the PE salt at 80° C. The crystallization commenced hereon at 75° C. After crystallization had finished, the mixture was filtered and the crystals were washed twice with 50 ml each of cold isopropyl acetate (chiral purity>99:1). The yellow PE salt was dried in vacuo at 50° C.

Yield: 42.0 g (87.5% of theory, ee %=98.7 (GC))

Release of the chiral 4-methyl-2-phenylthiazoline-4-carboxylic acid:

About 125 ml of 1 M HCl were slowly added to a vigorously stirred mixture of 42.0 g (0.12 mol) of chiral PE salt, 52.5 ml of water and 315 ml of MTBE, two clear phases being obtained. The HCl addition was carried out until the pH of the aqueous solution was 2–3. The organic phase was separated off and washed twice each with 105 ml of water. MTBE was stripped off from the organic phase, whereby the chiral 4-methyl-2-phenylthiazoline-4-carboxylic acid was obtained as a yellow oil, which crystallized overnight at room temperature.

Yield: 26.0 g (95.8% of theory)

Alternative to Stages 3 and 4:

As an alternative to stages 3 and 4, a resolution of 4-carbethoxy-4,5-dihydro-4-methyl-2-phenylthiazoline was carried out by means of lipase:

Preparation of a stock solution: 300 mg of 4-carbethoxy-4,5-dihydro-4-methyl-2-phenylthiazoline were taken up in 26 ml of phosphate buffer and dissolved by addition of 1 ml of DMF and 1 ml of isopropyl acetate. 2 ml of this stock solution were added to about 20 mg of *Candida rugosa* lipase and the mixture was stirred at room temperature for 24 hours.

After 4 hours, an ee of 70% was found by means of chiral GC at a yield of 79%, after 24 hours an ee of 99% (at 70% yield).

Inter alia, it was additionally possible to achieve similar results using *Candida antarctica* A, *Aspergillus* species protease and various CLECs.

5th Stage: Acidic hydrolysis to (S)-2-methylcysteine hydrochloride (variant a)

6.20 g (28.0 mmol) of 4-methyl-2-phenylthiazoline-4-carboxylic acid were dissolved in 65 ml of 6 M HCl (degassed by boiling twice in a nitrogen atmosphere). This solution was then refluxed for 16 h in a nitrogen atmosphere. After cooling to room temperature, the reaction mixture was filtered in order to separate off the precipitated benzoic acid (2.94 g=85.3%), which was washed twice with 10 ml each of degassed water. The HCl-acidic filtrate was then extracted three times with 30 ml each of MTBE. The aqueous phase was evaporated under reduced pressure to give an oil, which was dissolved twice in succession in 55 ml each of degassed water and always evaporated to an about 50% strength solution under reduced pressure. 150 ml of MTBE (degassed by boiling twice in a nitrogen atmosphere) were then added to this concentrated solution. The water was entrained by azeotropic distillation (water separator) at 52° C., an oil initially forming in the flask, which on further azeotroping broke down into a precipitate of (S)-2-methylcysteine hydrochloride. After removal of about 40 ml of MTBE by distillation and cooling of the suspension to 20° C., the (S)-2-methylcysteine hydrochloride was filtered off, washed twice with 20 ml each of MTBE and dried in vacuo (20 mbar) at 50° C.

Yield of (S)-2-methylcysteine hydrochloride: 4.10 g (85.0% of theory)

5th Stage: Acidic hydrolysis to (S)-2-methylcysteine hydrochloride (variant b)

18.6 g of 4-methyl-2-phenylthiazoline-4-carboxylic acid were dissolved in 186 ml of 6 N HCl under a nitrogen atmosphere and the solution was then heated under reflux for 16 hours. After cooling to 20° C., the precipitated benzoic acid was filtered off and washed with 2×10 ml of completely demineralized water. The filtrate was extracted three times with 95 ml each of MTBE, then residual MTBE was stripped off by evacuation at room temperature and only then was the water removed by distillation at reduced pressure and at most 40° C. The oil obtained was dissolved in 110 ml of water and again concentrated down to an about 50% strength solution. 300 ml of 2-butanol were added to this concentrated solution and the residual water was entrained by distilling off the azeotrope of 2-butanol and water (total: 250 ml). In the course of this, a water content of 0.6 gg % was achieved in the last distillate fraction. The concentrated solution obtained was further concentrated under reduced pressure, cooled to room temperature and then treated with 200 ml of MTBE. The precipitated crystals were filtered off with suction, washed 2× with 20 ml each of MTBE and dried at 45° C./30 mbar.

Yield: 13.62 g (94.5% of theory) Purity: 91.8 gg % (quant. NMR)

EXAMPLE 2

Preparation of (S)-2-methylcysteine·HCl (variant 2)
1st Stage—Acetonide Synthesis 50.0 g (0.27 mol) of L-cysteine ethyl ester hydrochloride were suspended in 500 ml of n-hexane and treated at room temperature with 31.4 g (0.54 mol) of acetone and 27.3 g (0.27 mol) of triethylamine. The reaction mixture was then heated to boiling on a water separator for 2 hours with separation of the water of reaction. The reaction mixture was cooled, the precipitate (triethylamine hydrochloride) was filtered off and washed with hexane, and the filtrate was freed of the solvent.

Yield of ethyl 2,2-dimethylthiazoline-4-carboxylate (acetonide):

48.6 g (95% of theory) of colorless oil; purity: 99.8 area % (GC)

2nd Stage—N-formylation 45 g (0.24 mol) of ethyl 2,2-dimethylthiazoline-4-carboxylate (acetonide) were dissolved in 450 g of formic acid, treated with 180 g of acetic anhydride (exothermic reaction) and stirred for one hour. The reaction mixture was concentrated on a Rotavapor and partitioned between MTBE and sodium hydrogencarbonate solution. The organic phase was dried azeotropically and then freed of the solvent.

Yield of ethyl 3-formyl-2,2-dimethylthiazoline-4-carboxylate:

51 g (98% of theory) of colorless oil Purity: 98.2 area % (GC)

3rd Stage—Methylation 12.1 g (120 mmol) of diisopropylamine were dissolved in 200 ml of MTBE under a nitrogen atmosphere, 28.1 g (110 mmol) of a 25% strength butyllithium solution in heptane were added dropwise to this solution at −20° C. and it was stirred for 20 minutes. 21.7 g (100 mmol) of ethyl 3-formyl-2,2-dimethylthiazoline-4-carboxylate in 100 ml of MTBE were added dropwise at −50° C. to the LDA solution prepared in this way in the course of half an hour. An orange suspension was formed in the course of this. After a reaction time of one hour, 7.4 ml (120 mmol) of methyl iodide in 40 ml of DMPU were added dropwise and the mixture was stirred at −50° C. for a further 1.5 hours and finally warmed to room temperature. The reaction mixture was treated with 125 ml of 1 N HCl and the phases were separated. The aqueous phase (pH 2.5) was extracted with 100 ml of MTBE and the combined organic phases were washed twice each with 100 ml of saturated sodium chloride solution. The organic phase was dried over sodium sulfate, filtered and the solvent was stripped off (21.5 g).

The residue was distilled at 140–145° C./4 mbar and the distillate (9.37 g), racemic ethyl 3-formyl-2,2,3-trimethylthiazoline-4-carboxylate, was purified by column chromatography on silica gel 60 using ethyl acetate:hexane= 1:5.

4th Stage—Resolution 161.4 mg of substrate (ethyl 3-formyl-2,2,3-trimethylthiazoline-4-carboxylate) were taken up in 12 ml of phosphate buffer and treated with 100 mg of DMF. After stirring for 7 min, a clear solution was obtained. 1.35 ml of this stock solution (corresponds to 18.83 mg of substrate) were added to the *Candida antarctica* "B" lipase and the reaction mixture was stirred at room temperature for 24 h. The product (3-formyl-2,2,3-trimethylthiazoline-4-carboxylic acid) was then isolated by extraction by means of MTBE with an ee of 80%.

5th Stage—Hydrolysis to (S)-2-methylcysteine·HCl 140 mg (0.6 mmol) of ethyl 3-formyl-2,2,4-trimethylthiazoline-4-carboxylate were heated to boiling in 5 ml of 5 N HCl for 20 hours, evaporated to dryness and then taken up again twice in 5 ml of water and evaporated again.

Yield: 100 mg of slightly yellow crystals of (S)-2-methylcysteine·HCl (~quantitative)

EXAMPLE 3

Preparation of 2,4-dihydroxybenzonitrile 50.0 g (0.362 mol, 1.0 eq) of 2,4-dihydroxybenzaldehyde and 180 ml of formic acid were added to a 500 ml Schmizo, whereby a brown suspension was achieved. 45.8 g (0.673 mol, 1.8 eq) of sodium formate were added as a batch in the course of 2 min, the temperature rising to 33° C. After the reaction mixture had been cooled again to 30° C., 35.6 g (0.217 mol, 1.2 eq) of hydroxylammonium sulfate were added in the course of 3 min, wherefrom a thick brown suspension resulted. After stirring at 30–32° C. for 10 min, this became a brown solution. During the subsequent warming to 100° C., crystallization commenced at 38° C. At 70° C., the crystal magma turned into a thin suspension, which was again stirrable. This reaction mixture was stirred at 100° C. for 2 h, and in the course of this the color changed to dark brown. An IPC (Memi-IP-4_01) and a TLC (silica gel 60 $F_{254}$, acetone:n-hexane:water 20:20:1) showed almost complete conversion. The formic acid was distilled off under reduced pressure (60° C., 10 mbar, 170 ml of distillate). The solid dark-brown residue was stirred in 400 ml of MTBE at 40° C. for 1 h. The insoluble residue (62.5 g) was filtered off and washed twice with 50 ml each of MTBE. 10 g of activated carbon (Norit CA 5) were added to the mother liquor and the mixture was refluxed for 1 h, filtered through Celite Super Hyflow at 40° C. and washed twice with 50 ml each of MTBE. The mother liquor was washed three times with 100 ml each of water. After the azeotropic removal of the water from the MTBE solution, it was concentrated to about 20% of the original volume under reduced pressure and 500 ml of toluene were added. The residual MTBE was then further stripped off. In the course of this, a brown precipitate deposited, which was filtered off. The toluene solution was then concentrated to a volume of about 150 ml, the 2,4-dihydroxybenzonitrile crystallizing out. This was filtered off, washed twice with 30 ml each of toluene and dried in vacuo (45° C., 20 mbar).

Yield of 2,4-dihydroxybenzonitrile: 34.5 g (70.5%, purity 97% (HPLC))

EXAMPLE 4

Coupling to 4,5-dihydro-2-(2,4-dihydroxyphenyl)-4-methylthiazole-4-(S)-carboxylic acid 4.00 g (23.3 mmol, 1.0 eq) of (S)-2-methylcysteine hydrochloride, prepared according to example 1, and 3.14 g (23.3 mmol, 1.0 eq) of 2,4-dihydroxybenzonitrile, prepared according to example 3, were suspended in 40 ml of ethanol (degassed by boiling twice in a nitrogen atmosphere) and 4.95 g (6.8 ml, 48.9 mmol, 2.05 eq) of triethylamine were added. The suspension obtained has a pH of 7.5–8.0 and was heated to reflux temperature for 20 h with stirring and under nitrogen. It was then cooled to 20° C. and ethanol was removed by distillation under reduced pressure, whereby an oil was obtained. This was dissolved in 50 ml of water, the pH was adjusted to pH 7.5 using about 1.0 ml of 20% strength KOH and the solution was extracted three times with 20 ml each of MTBE. The aqueous phase was separated off and adjusted to pH 12 using about 10.5 ml of 20% strength KOH. It was extracted four times with 20 ml each of MTBE until a triethylamine content of <0.1 area % (IPC (GC)) was achieved and then adjusted to pH 7.5 using about 3.4 ml of 6 M HCl. The MTBE was removed completely from the water phase by a distillation under reduced pressure (50° C., 200–45 mbar, 8 ml of distillate). The aqueous solution was acidified further to pH 1.5 using about 4.6 ml of 6 M HCl. In the course of this, 4,5-dihydro-2-(2,4-dihydroxyphenyl)-4-methylthiazole-4-(S)-carboxylic acid begins to crystallize out. This suspension was stirred at 15° C. for 1 h. The solid was filtered off, washed twice with 10 ml each of water (15° C.) and dried at 55° C. in vacuo (30 mbar).

Yield of 4,5-dihydro-2-(2,4-dihydroxyphenyl)-4-methylthiazole-4-(S)-carboxylic acid:

5.17 g (87.6% of theory, $^1$H-NMR showed no significant impurities)

EXAMPLE 5

Coupling to 4,5-dihydro-2-(2,4-dihydroxyphenyl)-4-methylthiazole-4-(S)-carboxylic acid 5.80 g of an ~80% strength solution of (S)-2-methylcysteine hydrochloride in 2-butanol (corresponds to 5.38 g or 25 mmol, 1.0 eq of pure substance) (prepared according to example 1, 5th stage, variant b, product solution before precipitation using MTBE) and 3.41 g (25 mmol, 1.0 eq) of 2,4-di-hydroxybenzonitrile, prepared according to example 3, were suspended in 55 ml of 2-butanol and 5.18 g (7.1 ml, 51.2 mmol, 2.05 eq) of triethylamine were added. The suspension obtained had a pH of 7.5 and was heated to reflux temperature for 20 h with stirring and under a nitrogen atmosphere. After 2 hours, the pH had fallen to 7.0, therefore a further 0.7 g (0.96 ml, 7 mmol, 0.25 eq) of triethylamine were added, whereupon a pH of 7.5 was established, which then remained stable. After a reaction time of 20 hours, the solvent was distilled off under reduced pressure, whereby an oil was obtained. This was dissolved in 50 ml of water, the pH was adjusted to pH 12.5 using 20.5 ml of 20% strength KOH and the solution was extracted three times using 30 ml each of MTBE. The aqueous phase was separated off and adjusted to pH 7 using 6.0 ml of 6 M HCl, then the MTBE was stripped off under reduced pressure (25–30° C., to 45 mbar). The aqueous solution was acidified further to pH 2 using 5.2 ml of 6 M HCl; in the course of this 4,5-dihydro-2-(2,4-dihydroxyphenyl)-4-methylthiazole-4-(S)-carboxylic acid began to crystallize out. This suspension was stirred at 20° C. for 1 h. The solid was filtered off, washed twice with 20 ml each of water and dried at 50° C. in vacuo (20 mbar).

Yield of 4,5-dihydro-2-(2,4-dihydroxyphenyl)-4-methylthiazole-4-(s)-carboxylic acid:

6.25 g (98.5% of theory, TLC showed no significant impurities).

What is claimed is:

1. A process for the preparation of substituted thiazolines of the formula (I)

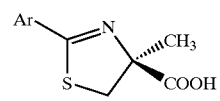

in which Ar is a phenyl, naphthyl, thienyl, pyridyl or quinolinyl radical which can optionally be substituted by one or more substituents from the group consisting of halogen, OH, benzyloxy, $C_1$–$C_4$-alkyl, $C_1$–$C_4$-alkoxy, COOR$_1$ where R$_1$ is H or $C_1$–$C_4$-alkyl, by coupling of (S)-α-methylcysteine hydrochloride of the formula (II)

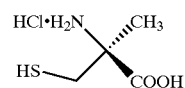

with an aromatic or heteroaromatic nitrile of the formula (III)

in which Ar is as defined above, or a corresponding $C_1$–$C_4$-alkyl imidate, which comprises reacting (S)-α-methylcysteine hydrochloride of the formula (II) in ethanol and/or butanol as solvent, containing 0.5 to 2 mol of a nitrile of the formula (III) or a corresponding $C_1$–$C_4$-alkyl imidate per mole of (S)-α-methylcysteine hydrochloride in the presence of 1.5 to 3 mol of a tertiary base per mole of (S)-α-methylcysteine hydrochloride at a pH of 6.5 to 10 at 50° C. up to the reflux temperature to give the corresponding thiazoline of the formula (I), which is isolated from the reaction mixture by removal of the solvent, extraction of the impurities and precipitation of the thiazoline by acidification.

2. The process as claimed in claim 1, wherein substituted thiazolines of the formula (I) are prepared in which Ar is a phenyl or naphthyl radical which can optionally be substituted by one or two substituents from the group consisting of OH, methyl, methoxy and COOH.

3. A process for the preparation of substituted thiazolines of the formula (I)

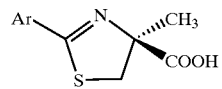

in which Ar is a phenyl or naphthyl radical which can optionally be substituted by one or two substituents from the group consisting of OH, methyl, methoxy and COOH, by coupling of (S)-α-methylcysteine hydrochloride of the formula (II)

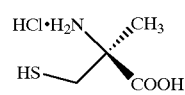

with an aromatic or heteroaromatic nitrile of the formula (III)

in which Ar is as defined above, or a corresponding $C_1$–$C_4$-alkyl imidate, which comprises reacting (S)-α-methylcysteine hydrochloride of the formula (II) in ethanol and/or butanol as solvent, containing 0.5 to 2 mol of a nitrile of the formula (III) or a corresponding $C_1$–C4-alkyl imidate per mole of (S)-α-methylcysteine hydrochloride in the presence of 1.5 to 3 mol of a tertiary base per mole of (S)-α-methylcysteine hydrochloride at a pH of 6.5 to 10 at 50° C. up to the reflux temperature to give the corresponding thiazoline of the formula (I), which is isolated from the reaction mixture by removal of the solvent, extraction of the impurities and precipitation of the thiazoline by acidification.

* * * * *